United States Patent [19]

Sorensen et al.

[11] Patent Number: 4,886,918

[45] Date of Patent: Dec. 12, 1989

[54] OLEFIN HYDRATION AND ETHERIFICATION PROCESS EMPLOYING SERIALLY STAGED OLEFIN INTRODUCTION

[75] Inventors: Charles M. Sorensen, Wilmington, Del.; Philip Varghese, Voorhees, N.J.

[73] Assignee: Mobil Oil Corporation, New York, N.Y.

[21] Appl. No.: 346,261

[22] Filed: May 3, 1989

Related U.S. Application Data

[63] Continuation of Ser. No. 270,406, Nov. 7, 1988, abandoned, which is a continuation of Ser. No. 150,187, Jan. 29, 1988, abandoned.

[51] Int. Cl.$^4$ .................... C07C 41/05; C07C 41/09
[52] U.S. Cl. .................... 568/697; 568/698; 568/897
[58] Field of Search .................... 568/697, 698, 867

[56] References Cited

U.S. PATENT DOCUMENTS

| | | |
|---|---|---|
| 2,162,913 | 6/1939 | Eversole et al. . |
| 2,477,380 | 7/1949 | Kreps et al. . |
| 2,797,247 | 6/1957 | Munster . |
| 2,798,097 | 7/1957 | Hettinger et al. . |
| 2,805,260 | 9/1957 | Keith . |
| 2,830,090 | 4/1958 | Teter et al. . |
| 2,861,045 | 11/1958 | Langer, Jr. . |
| 2,891,999 | 6/1959 | Langer, Jr. . |
| 3,006,970 | 10/1961 | Beuther et al. . |
| 3,198,752 | 8/1965 | Bridger et al. . |
| 3,810,849 | 5/1974 | Massie . |
| 3,989,762 | 11/1976 | Ester . |
| 4,042,633 | 8/1977 | Woods . |
| 4,175,210 | 11/1979 | Selwitz et al. . |
| 4,182,914 | 1/1980 | Imaizumi . |
| 4,214,107 | 7/1980 | Chang et al. . |
| 4,334,890 | 6/1982 | Kochar et al. . |
| 4,418,219 | 11/1983 | Hanes et al. . |
| 4,499,313 | 2/1985 | Okumura et al. . |
| 4,605,787 | 8/1986 | Chu et al. . |

FOREIGN PATENT DOCUMENTS

| | | |
|---|---|---|
| 0055045 | 6/1982 | European Pat. Off. . |
| 0210793 | 2/1987 | European Pat. Off. . |
| 133661 | 1/1979 | Fed. Rep. of Germany . |
| 25345 | 2/1984 | Japan . |

*Primary Examiner*—Howard T. Mars
*Attorney, Agent, or Firm*—Alexander J. McKillop; Charles J. Speciale; Malcolm D. Keen

[57] ABSTRACT

Light olefin is introduced at multiple points of entry into a conversion unit subdivided into first and second reaction zones. Reaction of olefin with water takes place in the first reaction zone under conditions intended to promote the production of alcohol therein and in the second reaction zone, alcohol produced in the first reaction zone is both dehydrated and reacted with olefin under conditions intended to promote the production of ether therein. The same or different shape selective acidic zeolites are employed as catalysts in both reaction zones.

25 Claims, 1 Drawing Sheet

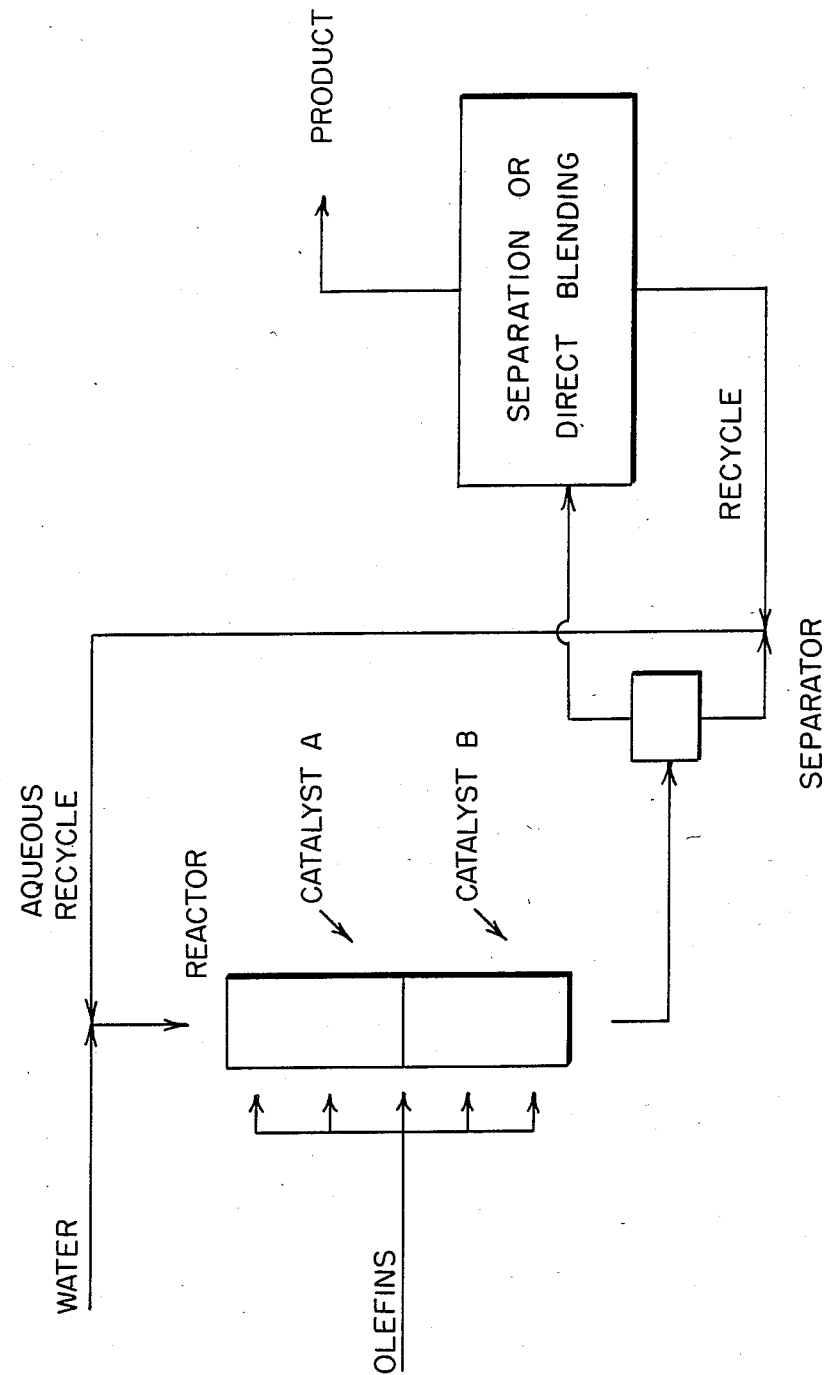

OLEFIN HYDRATION AND ETHERIFICATION PROCESS EMPLOYING SERIALLY STAGED OLEFIN INTRODUCTION

BACKGROUND OF THE INVENTION

This is a continuation of copending application Ser. No. 270,406, filed on Nov. 7, 1988, now abandoned, which is a continuation of copending application Ser. No. 150,187 filed on Jan. 29, 1988, now abandoned.

This invention relates to a process for the catalytic conversion of olefin(s) to provide ether(s) or mixtures of ether(s) and alcohol(s). More particularly, the invention relates to a process for the catalyzed hydration of a feed containing one or more light olefins such as ethylene, propylene, butenes, pentenes, hexenes, heptenes, etc., in a first reaction zone to provide alcohol(s) which are subsequently converted in a second reaction zone in the presence of freshly added olefin(s) to provide ethers, there being present in each reaction zone a shape selective acidic zeolite olefin catalyst which is effective for the conversion of olefin(s) therein. The ether(s) as well as their mixtures with alcohol(s) are useful, inter alia, as high octane blending stocks for gasoline.

There is a need for an efficient catalytic process to manufacture alcohols and ethers from light olefins thereby augmenting the supply of high octane blending stocks for gasoline. Lower molecular weight alcohols and ethers such as isopropyl alcohol (IPA) and diisopropyl ether (DIPE) are in the gasoline boiling range and are known to have a high blending octane number. In addition, by-product propylene from which IPA and DIPE can be made is usually available in a fuels refinery. The petrochemicals industry also produces mixtures of light olefin streams in the $C_2$ to $C_7$ molecular weight range and the conversion of such streams or fractions thereof to alcohols and/or ethers can also provide products useful as solvents and as blending stocks for gasoline.

The catalytic hydration of olefins to provide alcohols and ethers is a well-established art and is of significant commercial importance. Representative olefin hydration processes are disclosed in U.S. Pat. Nos. 2,162,913; 2,477,380; 2,797,247; 3,798,097; 2,805,260; 2,830,090; 2,861,045; 2,891,999; 3,006,970; 3,198,752; 3,810,849; 3,989,762, among others.

Olefin hydration employing zeolite catalysts is known. As disclosed in U.S. Pat. No. 4,214,107, lower olefins, in particular, propylene, are catalytically hydrated over a crystalline aluminosilicate zeolite catalyst having a silica to alumina ratio of at least 12 and a Constraint Index of from 1 to 12, e.g., acidic ZSM-5 type zeolite, to provide the corresponding alcohol, essentially free of ether and hydrocarbon by-product According to U.S. Pat. No. 4,499,313, an olefin is hydrated to the corresponding alcohol, in the presence of hydrogen-type mordenite or hydrogen-type zeolite Y each having a silica-alumina molar ratio of 20 to 500. The use of such a catalyst is said to result in higher yields of alcohol than olefin hydration processes which employ conventional solid acid catalysts. Use of the catalyst is said to offer the advantage over ion-exchange type olefin hydration catalysts of not being restricted by the hydration temperature. Reaction conditions employed in the process include a temperature of from 50°–300° C., preferably 100°–250 C., a pressure of 5 to 200 kg/cm$^2$ to maintain liquid phase or gas-liquid multiphase conditions and a mole ratio of water to olefin of from 1 to 20. The reaction time can be 20 minutes to 20 hours when operating batchwise and the liquid hourly space velocity (LHSV) is usually 0.1 to 10 in the case of continuous operation.

European patent application 210,793 describes an olefin hydration process employing a medium pore zeolite as hydration catalyst Specific catalysts mentioned are Theta-1, said to be preferred, ferrierite, ZSM-22, ZSM-23 and NU-10

The reaction of light olefins with alcohols to provide ethers is also a well known type of process. According to U.S. Pat. No. 4,042,633, diisopropylether (DIPE) is prepared from IPA employing montmorillonite clay catalysts, optionally in the presence of added propylene. U.S Pat. No. 4,175,210 discloses the use of silicatungstic acid as catalyst for the reaction of olefin(s) with alcohol to provide ether(s). As disclosed in U.S. Pat. No. 4,182,914, DIPE is produced from IPA and propylene in a series of operations employing a strongly acidic cation exchange resin as catalyst In the process for producing a gasoline blending stock described in U.S Pat. No. 4,334,890, a mixed $C_4$ stream containing isobutylene is reacted with aqueous ethanol to form a mixture of ethyl tertiary butyl ether and tertiary butanol U.S. Pat. No. 4,418,219 describes the preparation of methyl tertiary-butyl ether (MTBE), a high octane blending agent for motor fuels, by reacting isobutylene and methanol in the presence of boron phosphate, blue tungsten oxide or crystalline aluminosilicate zeolite having a silica to alumina mole ratio of at least 12:1 and a Constraint Index of from 1 to about 12 as catalyst. U.S. Pat. No. 4,605,787 discloses the preparation of alkyl tert-alkyl ethers such as MTBE and methyl tert-amyl ether (MTAE) by the reaction of a primary alcohol with an olefin having a double bond on a tertiary carbon atom employing as catalyst an acidic zeolite having a constraint index of from about 1 to 12, e.g., zeolite ZSM-5, 11, 12, 23 dealuminized zeolite Y and rare earth-exchanged zeolite Y. European patent application No. 55,045 describes a process for reacting an olefin and an alcohol to provide an ether, e.g., isobutene and methanol to provide MTBE, in the presence of an acidic zeolite such as zeolite Beta, zeolites ZSM-5, 8, 11, 12, 23, 35, 43 and 48 and others, as catalyst. Germany Pat. No. 133,661 describes the reaction of isobutene and methanol to provide a mixture of products including MTBE, butanol and isobutene dimer in the presence of acidic zeolite Y as catalyst. According to Japan Pat. No. 59-25345, a primary alcohol is reacted with a tertiary olefin in the presence of a zeolite having a silica to alumina mole ratio of at least 10 and the x-ray diffraction disclosed therein to provide a tertiary ether.

It is an object of the present invention to provide a process for converting low cost, readily available sources of light olefins to ether(s) and, optionally, mixtures of ether(s) and alcohol(s), which can be used, inter alia, as high octane blending stocks for gasoline.

It is a particular object of the invention to convert a light olefin or mixture of such olefins to ether(s) or mixture of alcohol(s) and ether(s) in an olefin conversion unit possessing first and second reaction zones, the first reaction zone containing a shape-selective acidic zeolite catalyst and operated under conditions favoring the production of alcohol(s) by the reaction of olefin(s) with water therein and the second reaction zone containing the same or a different shape-selective acidic zeolite catalyst and operated under conditions favoring the production of ether(s) by dehydration of alcohol(s) produced in the first reaction zone and by the reaction of such alcohol(s) with freshly added olefin(s) together with unconverted olefin(s) from the first reaction zone.

SUMMARY OF THE INVENTION

By way of realizing the foregoing and other objects of the invention, a process is provided for producing ether(s) alone or in admixture with alcohol(s) which comprises:

(a) introducing a feed containing a substantial amount of at least one light olefin into an olefin conversion unit possessing first and second interconnected reaction zones, said feed being introduced into each of said first and second reaction zones at at least one point of entry therein, said first and second reaction zones each containing a quantity of shape-selective acidic zeolite catalyst;

(b) introducing water into the first reaction zone and maintaining the zone under conditions conducive to the reaction of light olefin with water to produce alcohol therein;

(c) introducing at least a portion of the alcohol produced in the first reaction zone into the second reaction zone and maintaining the second reaction zone under conditions conducive to the dehydration of alcohol and the reaction of alcohol with light olefin to produce essentially pure ether or ether in admixture with alcohol therein.

Serially staged olefin introduction into the olefin conversion unit in accordance with the process of this invention serves two principal functions, namely, to provide olefin reactant for each of two minimum interconnected reaction zones and to serve as a quench for the exotherm occurring in the olefin conversion unit thereby facilitating temperature management for optimum production of olefin oxygenates. It is also within the scope of this invention to operate the olefin conversion unit with different shape-selective acidic zeolites in each reaction zone, each zeolite being chosen for its selectivity to alcohol or ether, whichever product is desired, in a particular zone.

BRIEF DESCRIPTION OF THE DRAWINGS

The FIGURE of drawing illustrates a schematic flow arrangement of an embodiment of the olefin hydration and etherification process herein.

DESCRIPTION OF THE PREFERRED EMBODIMENTS

The present invention is applicable to the conversion of individual light oefins and mixtures of olefins of various structures, preferably within the $C_{2-7}$ range, to ethers. Accordingly, the invention is applicable to the conversion of ethylene, propylene, butenes, pentenes, hexenes and heptenes, mixtures of these and other olefins such as gas plant off-gas containing ethylene and propylene, naphtha cracker off-gas containing light olefins, fluidized catalytic cracked (FCC) light gasoline containing pentenes, hexenes and heptenes, refinery FCC propane/propylene streams, etc.

For example, a typical FCC light olefin stream possesses the following composition:

| Typical Refinery FCC Light Olefin Composition | | |
|---|---|---|
| | Wt % | Mole % |
| Ethane | 3.3 | 5.1 |
| Ethylene | 0.7 | 1.2 |
| Propane | 14.5 | 15.3 |
| Propylene | 42.5 | 46.8 |
| Isobutene | 12.9 | 10.3 |
| n-Butane | 3.3 | 2.6 |
| Butenes | 22.1 | 18.3 |
| Pentanes | 0.7 | 0.4 |

The process of the invention is especially applicable to the conversion of propylene and propylene-containing streams to DIPE which may or may not contain IPA, the latter usually in minor quantities.

The conversion of the light olefin(s) takes place in an olefin conversion unit comprising a single reactor subdivided into a series of interconnected reaction zones, each zone containing a quantity of shape-selective acidic zeolite of which more will be said later. The reactor possesses a minimum of two such reaction zones, the first reaction zone where reaction of olefin with water to produce alcohol largely occurs and the second reaction zone where dehydration of alcohol according to the reaction

and reaction of alcohol with olefin according to the reaction

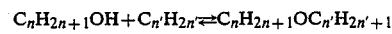

to product ether largely occur.

The olefin conversion unit may also possess one or more intermediate reaction zones interposed between the first and second reaction zones. These optional reaction zones also contain shape-selective acidic zeolite catalyst and can be operated in a manner intended to emphasize the production of alcohol(s) or ether(s).

Alternatively, the conversion of olefin(s) to ether(s) can take place in a series of individual reactors any ones of which may or may not be subdivided into distinct reaction zones as in the case of the single reactor, multi-reaction zone embodiment. Each reactor in the series will be operated in a manner intended to emphasize the production of alcohol(s) or ether(s), the ultimate object being production of ether(s) in the last reactor in the series to provide an overall high percentage of olefin conversion.

Whether the olefin conversion unit is a single multi-reaction zone reactor or series of individual reactors, each conversion operation, i.e., the hydration of olefin to produce alcohol, the dehydration of alcohol to produce ether and the reaction of olefin with alcohol to produce ether, can be carried out under liquid phase, vapor phase or mixed vapor-liquid phase conditions in batch or in a continuous manner under stirred tank reactor or fixed bed flow reactor conditions, e.g., trickle-bed, liquid-up-flow, liquid-down-flow, counter-current flow, co-current flow, etc. Olefin, preferably at or below ambient temperature, is separately introduced into the first and second reaction zones and, where present, into one or more of the aforesaid intermediate reaction zones. It is also within the scope of the present invention to recover and recycle unreacted water, olefin and/or product alcohol(s) to selected reaction zone(s)

The catalyst employed in both the olefin hydration and the etherification operations as well as in the optional intermediate reaction zones is the same or different shape-selective acidic zeolite. In general, the useful catalysts embrace two categories of zeolite, namely, the intermediate pore size variety as represented, for example, by ZSM-5, which possess a Constraint Index of greater than about 2 and the large pore variety as represented, for example, by zeolites Y and Beta, which possess a Constraint index no greater than about 2. Both varieties of zeolites will possess a framework silica-to-alumina ratio of greater than about 7.

For purposes of this invention, the term "zeolite" is meant to include the class of porotectosilicates, i.e , porous crystalline silicates, which contain silicon and oxygen atoms as the major components. Other components can be present in minor amounts, usually less than 14 mole %, and preferably less than 4 mole %. These components include aluminum, gallium, iron, boron, and the like, with aluminum being preferred. The minor components can be present separately or in mixtures in the catalyst. They can also be present intrinsically in the framework structure of the catalyst.

The framework silica-to-alumina mole ratio referred to can be determined by conventional analysis. This ratio is meant to represent, as closely as possible, the mole ratio of silica to alumina in the rigid anionic framework of the zeolite crystal and to exclude any alumina which may be present in a binder material optionally associated with the zeolite or present in cationic or other form within the channels of the zeolite. Although zeolites with a silica-to-alumina mole ratio of as low as about 7 are useful, it is preferred to use zeolites having much higher silica-to-alumina mole ratios, i.e., ratios of at least about 20:1 and preferably greater than about 200:1, e.g., 500:1, and even higher. In addition zeolites as otherwise characterized herein but which are substantially free of aluminum, i.e , having silica-to-alumina mole ratios up to and including infinity, are useful and can even be preferable in some cases. The useful class of zeolites, after activation, acquire an intra-crystalline sorption affinity for normal hexane which is greater than that for water, i.e., they exhibit "hydrophobic" properties. A convenient measure of the extent to which a zeolite provides controlled access to molecules of varying sizes to its internal structure is the aforementioned Constraint Index of the zeolite. A zeolite which provides relatively restricted access to, and egress from, its internal structure is characterized by a relatively high value for the Constraint Index, i.e., above about 2. On the other hand, zeolites which provide relatively free access to the internal zeolitic structure have a relatively low value for the Constraint Index, i.e., about 2 or less. The method by which Constraint Index is determined is described fully in U.S. Pat. No. 4,016,218, to which reference is made for details of the method.

Constraint Index (CI) values for some zeolites which can be used in the process of this invention are:

| Zeolite | Constraint Index (At Test Temperature) |
| --- | --- |
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-35 | 4.5 (454° C.) |
| ZSM-38 | 2 (510° C.) |

-continued

| Zeolite | Constraint Index (At Test Temperature) |
| --- | --- |
| ZSM-48 | 3.5 (538° C.) |
| ZSM-50 | 2.1 (427° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Zeolite Beta | 0.6–2.0 (316° C.–399° C.) |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables, such as crystal size of the zeolite, the presence of occluded contaminants, etc., can affect the Constraint Index. Therefore, it will be appreciated that it may be possible to so select test conditions, e.g., temperatures, as to establish more than one value for the Constraint Index of a particular zeolite. This explains the range of Constraint Indices for zeolite Beta Useful zeolite catalysts of the intermediate pore size variety, and possessing a Constraint Index of greater than about 2 up to about 12, include such materials as ZSM-5, ZSM-11, ZSM-23, ZSM-35 and ZSM-38.

ZSM-5 is more particularly described in U.S. Pat. No. Re. 28,341 (of original U.S. Pat. No. 3,702,886), the entire contents of which are incorporated herein by reference.

ZSM-11 is more particularly described in U.S. Pat. No. 3,709,979, the entire contents of which are incorporated herein by reference.

ZSM-23 is more particularly described in U.S. Pat. No. 4,076,842, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference. Although ZSM-38 possesses a Constraint Index of 2.0, it is often classified with the intermediate pore size zeolites and will therefore be regarded as such for purposes of this invention.

The large pore zeolites which are useful as catalysts in the process of this invention, i.e., those zeolites having a Constraint Index of no greater than about 2, are well known to the art Representative of these zeolites are zeolite Beta, zeolite X, zeolite L, zeolite Y, ultrastable zeolite Y (USY), dealuminized Y (Deal Y), rare earth-exchanged zeolite Y (REY), rare earth-exchanged dealuminized Y (RE Deal Y), mordenite, ZSM-3, ZSM-4, ZSM-12, ZSM-20 and ZSM-50 and mixtures of any of the foregoing. Although zeolite Beta has a Constraint Index of about 2 or less, it should be noted that this zeolite does not behave exactly like other large pore zeolites. However, zeolite Beta does satisfy the requirements for a catalyst of the present invention.

Zeolite Beta is described in U.S. Pat. No. Re. 28,341 (of original U.S. Pat. No. 3,308,069), to which reference is made for details of this catalyst.

Zeolite X is described in U.S. Pat. No. 2,882,244, to which reference is made for the details of this catalyst.

Zeolite L is described in U.S. Pat. No. 3,216,789, to which reference is made for the details of this catalyst.

Zeolite Y is described in U.S. Pat. No. 3,130,007, to which reference is made for details of this catalyst.

Low sodium ultrastable zeolite Y (USY) is described in U.S. Pat. Nos. 3,293,192, 3,354,077, 3,375,065, 3,402,996, 3,449,070 and 3,595,611, to which reference is made for details of this catalyst.

Dealuminized zeolite Y (Deal Y) can be prepared by the method found in U.S. Pat. No. 3,442,795, to which reference is made for details of this catalyst.

Zeolite ZSM-3 is described in U S. Pat. No. 3,415,736, to which reference is made for details of this catalyst.

Zeolite ZSM-4 is described in U.S. Pat. No. 3,923,639, to which reference is made for details of this catalyst.

Zeolite ZSM-12 is described in U.S. Pat. No. 3,832,449, to which reference is made for the details of this catalyst.

Zeolite ZSM-20 is described in U.S. Pat. No. 3,972,983, to which reference is made for the details of this catalyst.

Zeolite ZSM-50 is described in U.S. Pat. No. 4,640,829 to which reference is made for details of this catalyst.

Also included within the definition of the useful zeolites are crystalline porous silicoaluminophosphates such as those disclosed in U.S. Pat. No. 4,440,871, the catalytic behavior of which is similar to that of the aluminosilicate zeolites The zeolite(s) selected for use herein will generally possess an alpha value of at least about 1, preferably at least 10 and more preferably at least about 100. "Alpha value", or "alpha number", is a measure of zeolite acidic functionality and is more fully described together with details of its measurement in U.S. Pat. No. 4,016,218, J. Catalysis, 6, pp. 278-287 -(1966) and J. Catalysis 61. pp. 390-396 (1980). Zeolites of low acidity (alpha values less than about 200) can be achieved by a variety of techniques including (a) synthesizing a zeolite with a high silica/alumina ratio, (b) steaming, (c) steaming followed by dealuminization and (d) substituting framework aluminum with other species. For example, in the case of steaming, the zeolite(s) can be exposed to steam at elevated temperatures ranging from about 500° to about 1200° F. and preferably from about 750° to about 1000° F. This treatment can be accomplished in an atmosphere of 100% steam or an atmosphere consisting of steam and a gas which is substantially inert to the zeolite. A similar treatment can be accomplished at lower temperatures employing elevated pressure, e.g., at from about 350° to about 700° F. with from about 10 to about 200 atmospheres. Specific details of several steaming procedures may be gained from the disclosures of U.S. Pat. Nos. 4,325,994, 4,374,296 and 4,418,235, the contents of which are incorporated by reference herein. Aside from, or in addition to any of the foregoing procedures, the surface acidity of the zeolite(s) can be eliminated or reduced by treatment with bulky reagents as described in U.S. Pat. No. 4,520,221, the contents of which are incorporated by reference herein.

In practicing the olefin hydration and etherification process of the present invention, it can be advantageous to incorporate the zeolite(s) into some other material, i.e., a matrix or binder, which is resistant to the temperature and other conditions employed in the process. Useful matrix materials include both synthetic and naturally-occurring substances, e.g., inorganic materials such as clay, silica and/or metal oxides. Such materials can be either naturally-occurring or can be obtained as gelatinous precipitates or gels including mixtures of silica and metal oxides. Naturally-occurring clays which can be composited with the zeolite include those of the montmorillonite and kaolin families, which families include the sub-bentonites and the kaolins commonly known as Dixie, McNamee-Georgia and Florida clays or others in which the main mineral constituent is haloysite, kaolinite, dickite, nacrite or anauxite. Such clays can be used in the raw state as originally mined or initially subjected to calcination, acid treatment or chemical modification.

In addition to the foregoing materials, the zeolite(s) employed herein can be composited with a porous matrix material such as carbon alumina, titania, zirconia, silica, silica-alumina, silica-magnesia, silica-zirconia, silica-thoria, silica-beryllia, silica-titania, etc., as well as ternary oxide composition, such as silica-alumina-thoria, silica-alumina-zirconia, silica-alumina-magnesia, silica-magnesia-zirconia, etc.. The matrix can be in the form of a cogel. The relative proportions of zeolite component(s) and matrix material, on an anhydrous basis, can vary widely with the zeolite content ranging from between 1 to about 99 wt %, and more usually in the range of about 5 to about 90 wt % of the dry composite In some cases, it may be advantageous to provide the zeolite hydration etherification catalyst(s) in the form of an extrudate bound with a low acidity refractory oxide binder employing the method described in commonly assigned, copending U.S. patent application Ser. No. 44,639, filed May , 1987, the contents of which are incorporated by reference herein. In accordance with said method, zeolite, water and a low acidity refractory oxide binder, e.g., silica, which contains at least an extrusion-facilitating amount of the binder in a colloidal state and which is substantially free of added alkali metal base and/or basic salt, is formed into an extrudable mass, the mass is extruded and the resulting extrudate is dried and calcined.

The original cations associated with the zeolite(s) utilized herein can be replaced by a wide variety of other cations according to techniques well known in the art, e.g., by ion-exchange. Typical replacing cations include hydrogen, ammonium, alkyl ammonium and metal cations, and their mixtures. Metal cations can also be introduced into the zeolite. In the case of metal cations, particular preference is given to metals of Groups IB to VIII of the Periodic Table, including, by way of example, iron, nickel, cobalt, copper, zinc, palladium, calcium, chromium, tungsten, molybdenum, rare earth metals, etc. These metals can also be present in the form of their oxides.

A typical ion-exchange technique involves contacting the particular zeolite with a salt of the desired replacing cation. Although a wide variety of salts can be employed, particular preference is given to chlorides, nitrates and sulfates. Representative ion-exchange techniques are disclosed in a number of patents including U.S. Pat. Nos. 3,140,249, 3,140,251 and 3,140,253.

Following contact with a solution of the desired replacing cation, the zeolite is then preferably washed with water and dried at a temperature ranging from about 1150° to about 600° F. and thereafter calcined in air or other inert gas at temperatures ranging from about 500° to about 1500° F. for periods of time ranging from about 1 to about 48 hours or more.

As previously stated, each reaction zone will ordinarily be operated under conditions which are conducive to the conversion of reactant(s) to particular product(s) therein. In the case of the first reaction zone, conditions will be selected which will favor the production of alcohol, with or without the coproduction of some ether(s), and in the second reaction zone, conditions will be chosen which will tend to maximize the production of ether, with or without the coproduction of some alcohol(s). It has been observed that catalyst selection and water:olefin mole ratio are particularly significant process parameters herein.

The Conditions in the First (i.e., Primarily Alcohol-producing Reaction Zone)

Certain zeolites are known, or have been found, to be especially effective for the catalysis of the olefin hydration reaction to produce little, if any, by-product ether and oligomer, especially at low water to olefin mole ratios, e.g., below about 1. As described in U.S. Pat. No. 4,214,107 referred to, supra, acidic ZSM-5, an intermediate pore size zeolite, has been demonstrated to be effective in converting propylene to isopropanol with essentially no coproduction of diisopropyl ether. Other intermediate pore size zeolites identified in U.S. Pat. No. 4,214,107 as generally useful for the hydration of $C_{2-4}$ monoolefins to provide substantially ether-free alcohols are ZSM-11, ZSM-12, ZSM-35 and ZSM-38. These zeolites can also be used to good effect in the first reaction zone of the process herein Of this group of zeolites, an especially preferred hydration catalyst for use in the first reaction zone is acidic ZSM-35 which, as disclosed in commonly assigned, copending U.S. patent application Ser. No. 139,565, the contents of which are incorporated by reference herein, provides a much greater percentage of propylene conversion to isopropyl alcohol compared to that provided by acidic ZSM-5 under comparable hydration conditions, particularly when the water:propylene mole ratio is less than about 1.

Other useful catalysts for use in the first reaction zone include the large pore zeolites such as those mentioned above (i.e., zeolite Beta, X, L, Y, USY, REY, Deal Y, ZSM-3, ZSM-4, ZSM-12, ZSM-20 and ZSM-50) as disclosed in commonly assigned, concurrently filed U.S. patent application Ser. No. 139,567. In accordance with said application, these large pore zeolite catalysts are used to effect the conversion of light olefin(s) to a mixture of alcohol(s) and ether(s) by contacting the olefin(s) with water in the vapor and/or liquid phase at a temperature of from about 100° to 230° C., preferably from about 120° to about 220° C. and most preferably from about 140° to about 200° C., a total system pressure of at least about 5 atm, preferably at least about 20 atm and more preferably at least about 40 atm, a water to total olefin mole ratio of from 0.1 to less than about 1.0, preferably from about 0.2 to 0.8 and most preferably from about 0.3 to 0.7 and an LHSV of from about 0.1 to about 10 in the presence of an acidic form of the zeolite. In the specific case of acidic zeolite Beta, and as described in commonly assigned, concurrently filed U.S. patent application Ser. No. 139,570, the contents of which are incorporated herein, the hydration conditions need not be so limited as those stated above for the case of large pore zeolites generally. Thus, use of acidic zeolite Beta can be accompanied by essentially any practical set of hydration conditions which provides alcohol(s) (and usually ether(s) as well) in appreciable amounts. As disclosed in said application, good results can generally be obtained employing a temperature ranging from ambient up to about 300° C., preferably from about 50° to about 220° C. and more preferably from about 90° to about 200° C., a total system pressure of at least about 5 atm, preferably at least about 20 atm and more preferably at least about 40 atm, a water to total olefin mole ratio of from about 0.1 to about 30, preferably from about 0.2 to about 15 and most preferably from about 0.3 to about 5, and an LHSV of from about 0.1 to about 10. It should be noted, however, that at the unusually low water:olefin mole ratios of U.S. patent application Ser. No. 139,567, the production of olefin hydration products employing zeolite Beta as catalyst shifts toward ether(s) and away from alcohol(s). Such being the case, zeolite Beta, in addition to being useful in the first reaction zone under relatively high water to total olefin mole ratio conditions to emphasize alcohol production, can also be advantageously employed in the second reaction zone under relatively low water to total olefin mole ratios to emphasize ether production.

As stated earlier, olefin is introduced into each reaction zone at at least one point of entry and can be introduced in a reaction zone at multiple points of entry. In the case of the latter, the water:olefin mole ratios can be regarded as average, or overall, mole ratios of those given herein. In addition to being introduced into the first reaction zone, water can also be introduced at one or more points of entry into this zone and/or at one or more points of entry into any other reaction zone(s) comprising the olefin conversion unit. As in the case of multiple points of olefin introduction in a single reaction zone, where water is introduced at more than one point of entry in a given zone, the water:olefin ratio for such reaction zone can be viewed as an overall ratio for the zone.

Since water and olefin serve both as reactants and as heat quench media in the process of this invention, the overall water:olefin mole ratio for a particular reaction zone will be selected in accordance with whether alcohol or ether is to be the predominant product in the zone and the exothermic profile of the zone. These factors are in turn influenced by the nature of the olefin feed, the choice of catalyst and other operational parameters, and can be readily determined in a given case by routine experimentation.

The Conditions in the Second (i.e., Primarily Ether-producing) Reaction Zone

In general, any of the acidic zeolites known to be useful for the catalysis of the reaction of olefin(s) and alcohol(s) to provide ether(s) can be suitably employed in the second reaction zone herein. These include the zeolites described in U.S. Pat. No. 4,605,787, the contents of which are incorporated by reference herein Such zeolites include the intermediate pore size zeolites ZSM-5, ZSM-11 and ZSM-23 and the large pore zeolites Y, REY, Deal Y, RE Deal Y and ZSM-12 referred to supra. As indicated above, at low water to olefin mole pressures, zeolite Beta is especially advantageous for use in the second reaction zone.

The reaction conditions of the second reaction zone are desirably maintained within the ranges of temperature, pressure, liquid hourly space velocity and water-:olefin mole ratios disclosed above in connection with the operation of the first reaction zone and can be the same or different from those employed in the operation of the latter zone.

Where a mixture of alcohol(s) and ether(s) are produced in accordance with this invention and it is desired to recover the ether(s) in essentially pure form or containing at most a few percent of co-produced alcohol(s), it can be advantageous to employ the ether recovery processes of commonly assigned, concurrently filed U.S. patent application Ser. Nos. 139,543 and 139,566 the contents of which are incorporated by reference herein.

According to U.S. patent application Ser. No. 139,543 as applied to the production of DIPE as well as mixtures of IPA and DIPE in predetermined ratios, a mixture of IPA and DIPE produced in the olefin conversion unit (in the case of the present process, the second, or etherification, reaction zone) is introduced to a distillation unit where an azeotropic mixture of IPA, DIPE, water and propylene oligomers (mostly $C_6$ olefin) is distilled off and, following cooling, is introduced into a decanter in which phase separation takes place. The upper layer contains mostly DIPE, e.g., 90 weight percent or more, and relatively little water, e.g., 1 weight percent or so. The lower layer is largely water containing negligible quantities of IPA and DIPE. The quantity of the decanter overhead which is recycled can be regulated so as to control the water content in the final product. The bottoms fraction from the distillation unit, mainly IPA, can be recombined with DIPE in the decanter overhead to provide an IPA/DIPE mixture of predetermined composition. In addition or in the alternative, the IPA from the distillation unit can be recycled to the olefin conversion unit (preferably to the second reaction zone in the case of the present invention).

According to U.S. patent application Ser. No. 139,566, again, as applied to the recovery of DIPE from an IPA/DIPE mixture, the mixture is introduced to a distillation unit operated at or below atmospheric pressure to effect further purification of the DIPE. The azeotropic IPA, DIPE and water overhead product containing a small amount of propylene oligomer is condensed and thereafter contacted with reactor feed water The resulting phase separation provides a DIPE product containing at most negligible amounts of IPA and water, e.g., 1.0 weight percent and 0.5 weight percent of these materials, respectively. The remaining aqueous phase can be recycled to the olefin conversion unit.

The invention will now be described in connection with the following example illustrating the conversion of propylene to a mixture of PPA and DIPE.

EXAMPLE

A multi-bed propylene conversion unit is provided with two reaction zones, Zone A (hydration zone) and Zone B (etherification zone), featuring multiple points of olefin introduction as schematically shown in the appended FIGURE of drawing. Zone A contains ZSM-35 and is operated under conditions which maximize the conversion of propylene to IPA with little if any co-production of DIPE or oligomer. Zone B contains zeolite Beta and is operated under conditions which maximize the conversion of IPA produced in zone A and unconverted as well as freshly added propylene to DIPE.

The reaction conditions of zones A and B are maintained as follows:

| Reaction Conditions | Zone A | Zone B |
|---|---|---|
| Temperature | 330° F. | 330° F. |
| Pressure | 1000 psig | 1000 psig |
| LHSV | 0.9 | 0.6 |
| Overall Mole Ratio of Reactants | 0.5:1 water to propylene | 1.1:2.2:1.0 water to propylene to IPA mole ratios |

Under the foregoing conditions, Zone A will provide a reaction effluent made up of unconverted propylene, water and IPA at propylene conversion rates of 30 weight percent or more. This effluent, combined with additional propylene feed, will undergo conversion in Zone B under the stated conditions to provide a mixture of IPA and DIPE (predominantly the latter) containing 1 wt. % or less of oligomer The IPA/DIPE mixture produced in Zone B is conveyed to a high pressure separator operating below reaction temperature There, two liquid phases form, the aqueous phase being recycled to Zone A and the organic phase, containing IPA, DIPE and small amounts of water, unreacted propylene and oligomer, is subjected to one or more other separation operations (e.g., the ether recovery processes of either of U.S. patent application Ser. Nos. 139,543 and 139,566 described, supra) to provide an oxygenate produce of desired properties. Alternatively, the product mixture can be blended directly with a base gasoline stock to increase its octane rating with the aqueous layer being recycled to Zone A together with the aqueous phase from the high pressure separator.

What is claimed is:

1. A process for producing ether(s) or mixture of ether(s) and alcohol(s) which comprises:
   (a) introducing a feed containing a substantial amount of at least one light olefin into an olefin conversion unit possessing first and second interconnected reaction zones, said feed being introduced into each of said first and second reaction zones at at least one point of entry therein, said first and second reaction zones each containing a quantity of shape-selective acidic zeolite catalyst;
   (b) introducing water into the first reaction zone and maintaining the zone under conditions conducive to the reaction of light olefin with water to produce alcohol therein;
   (c) introducing at least a portion of the alcohol produced in the first reaction zone into the second reaction zone and maintaining the second reaction zone under conditions conducive to the dehydration of alcohol and the reaction of alcohol with light olefin to produce essentially pure ether or ether in admixture with alcohol therein.

2. The process of claim 1 wherein the zeolite in each reaction zone is the same or different zeolite selected from the group consisting of zeolites possessing a Constraint Index of above about 2 to about 12 and zeolites possessing a Constraint Index of about 2 or less.

3. The process of claim 2 wherein the zeolite in each reaction zone is the same or different zeolite selected from the group consisting of zeolites ZSM-5, ZSM-11, ZSM-23, ZSM-35, ZSM-38, Beta, X, L, Y, USY, REY, Deal Y, Re Deal Y, ZSM-3, ZSM-4, ZSM-12, ZSM-20 and ZSM-50.

4. The process of claim 1 wherein the zeolite in the first reaction zone is selected from the group consisting of zeolites ZSM-5, ZSM-11, ZSM-23, ZSM-35 and ZSM-38 and the zeolite in the second reaction zone is selected from the group consisting of zeolites Beta, X, L, Y, USY, REY, Deal Y, RE Deal Y, ZSM-3, ZSM-4, ZSM-12, ZSM-20; and ZSM-50.

5. The process of claim 1 wherein the olefin feed contains a mixture of light olefins.

6. The process of claim 1 wherein the olefin component of the feed contains from two to seven carbon atoms.

7. The process of claim 1 wherein the olefin feed contains at least one olefin selected from the group consisting of ethylene, propylene, butenes, pentenes, hexenes and heptenes.

8. The process of claim 1 wherein the olefin feed is gas plant off-gas containing ethylene and propylene.

9. The process of claim 1 wherein the olefin feed is naphtha cracker off-gas containing light olefins.

10. The process of claim 1 wherein the olefin feed is light catalytic cracked gasoline containing pentenes, hexenes and heptenes.

11. The process of claim 1 wherein the temperature in the first and/or second reaction zone is from about 50° to about 300° C.

12. The process of claim 1 wherein the temperature in the first and second reaction zone is from about 90° to about 220° C.

13. The process of claim 1 wherein the temperature in the first and/or second reaction zone is from about 110° to about 200° C.

14. The process of claim 1 wherein the total system pressure in the first and/or second reaction zone is at least about 5 atm.

15. The process of claim 1 wherein the total system pressure in the first and/or second reaction zone is at least about 20 atm.

16. The process of claim 1 wherein the total system pressure in the first and/or second reaction zone is at least about 40 atm.

17. The process of claim 1 wherein the overall mole ratio of water to total olefin in the first and/or second reaction zone is from about 0.1 to about 30.

18. The process of claim 1 wherein the overall mole ratio of water to total olefin in the first and/or second reaction zone is from about 0.2 to about 15.

19. The process of claim 1 wherein the overall mole ratio of water to total olefin in the fist and/or second reaction zone is from about 0.3 to about 5.

20. The process of claim 1 wherein the LHSV in the first and/or second reaction zone is from about 0.1 to about 10.

21. The process of claim 1 wherein the zeolite catalyst in either or both reaction zones is composited with a binder.

22. The process of claim 1 wherein the zeolite catalyst in either or both reaction zones is composited with alumina or silica as binder.

23. The process of claim 1 wherein the zeolite catalyst in either or both reaction zones is composited with at least an extrusion-facilitating amount of a low acidity refractory oxide binder in a colloidal state and which is substantially free of alkali metal base and/or basic salt.

24. The process of claim 1 wherein product alcohol(s) are recovered and introduced into at least one reaction zone.

25. The process of claim 1 wherein product alcohol(s) are recovered and introduced into the second reaction zone.

* * * * *